United States Patent [19]

Kirsch

[11] Plant 4,428

[45] Jun. 12, 1979

[54] LILY NAMED GOLD NUGGET

[76] Inventor: Ted T. Kirsch, Sitkum Rt. Box 142, Myrtle Point, Oreg. 97458

[21] Appl. No.: 926,911

[22] Filed: Jul. 20, 1978

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler & Snow

[57] ABSTRACT

A new variety of lily plant of the chalice-type Asiatic Hybrid particularly distinguished by the gold coloring of its five to six inch diameter flowers which are borne in raceme arrangement on tall strong stems and strong upright pedicels, usually with one bud or flower on each pedicel, and by its habit of forming aerial bulbils in the leaf axils at blooming time.

1 Drawing Figure

BACKGROUND OF THE NEW PLANT

My new lily plant originated as a seedling of unknown parentage growing at my nursery in Arcata, Calif. Its similarity to the variety "Yellow Jewel" (U.S. Plant Pat. No. 3,805) prompted me to propagate this new plant for study with the result that I have found advantageous and distinctive characteristics in the new plant which makes it a valuable addition to the field of commercial lily plant culture. Propagation of this new lily through successive generations by means of scales and tissue culture at Arcata, Calif., has shown that its distinctive characteristics hold true from generation to generation and appear to be firmly fixed.

DESCRIPTION OF THE DRAWING

This new variety of lily plant is illustrated by the accompanying photographic drawing which, in full color, shows a full grown blooming plant in the upper view and a closeup view of several blooms in the lower view. The color rendition is as nearly true as can be reasonably obtained by conventional photographic procedures.

DESCRIPTION OF THE NEW PLANT

The following is a detailed description of my new variety of lily as observed at Arcata, Calif., with color designations according to the R.H.S. Colour Chart published by The Royal Horticultural Society of London, England.

THE PLANT

Origin: Seedling.
Parentage: Unknown.
Classification: Asiatic Hybrid, Chalice-Type.
Form: Tall and a single stem from each bulb.
Height: One to three feet, depending upon the age of the bulb.
Growth: Upright and sturdy, with excellent strength.
Stem Size: About ¼ inch diameter at about one foot in height to about ¾ inch diameter at about 3 feet.
Foliage: Abundant in quantity.
*Size of leaf.*—2 to 4 inches long and ½ to 1 inch wide on the stem; at flower cluster, the leaves are 3 in number and 1½ to 2¾ inches long and 1 to 1¼ inches wide.
*Shape of leaf.*—Lanceolate.

*Texture.*—Leathery.
*Aspect.*—Smooth.
Aerial bulbils: Produced in the leaf axils.
*Size.*—About ⅛ to ¼ inch in diameter.
*Color.*—Maroon.
Stem bulblets (under ground):
*Occurrence.*—4 to 12 on each healthy normal plant at digging time.
*Size.*—About ¼ to 1 inch in diameter.
*Color.*—White.
Bulbs: Size — About 1 to 3 inches in diameter.
*Color.*—White.

THE BUD

Form: Elongate-oblong with an obtuse apex.
Size: About 2 to 3 inches long and ½ to ¾ inch in diameter.
Opening: Normal, tertiary and secondary buds opening successively.
Color: Greenish-Yellow when sepals first divide and petals begin to unfurl.
Pedicel: Strong and generally upright, angled about 30 degrees from vertical.
*Length.*—3 to 5 inches.
*Number of buds.*—Usually one, occasionally two.

THE FLOWER

Blooming habit: Annually, and profusely in June or early July.
Size of flower: Medium, averaging 5 to 6 inches in diameter and about 1 inch in depth.
Borne: From large bulbs the inflorescence has a raceme arrangement for the first 2 or 3 pedicels (each having 1 or 2 buds) and then, at the top, breaks into an umbel cluster of 2 to 8 pedicels with one bloom on each. Small bulbs often produce an umbel cluster only, each pedicel having a single bloom. The size of the bulb and its cultural care will determine the number of buds and blooms to be found on a particular inflorescence. From large bulbs this plant may produce 6 to 8 open blooms at the same time on each pedicel and 2 or 3 open blooms on the top umbel cluster.
Shape: Generally slightly cupped with uniformly spaced petals in star arrangement, with the edges of the petals curving slightly inward.
Petalage: Normal, 3 sepals and 3 petals.
*Form.*—Elliptical, with obtuse apex, prominent nectariferous grooves and a central longitudinal furrow bisecting each petal. The petals are about 1 to 1¼ inches in width and the edges are entire.

*Color.*—Upper side — Yellow 7B upon opening, with a Dark Green nectariferous groove having Light Green margins fading into Light Greenish-Yellow in the base portion of the petals. The petals will always have 3 to 12 dark "pepper spots". Under side — Yellow, near 7B. Note: The flower color may vary, either lighter or darker, according to the soil and climate in which the plant is grown.

*Papillae.*—Present on the petals and from 4 to 8 in number.

*Texture.*—Leathery.

*Aspect.*—Velvety.

Discoloration: Flower color becomes darker as blossom matures.

Effect of weather: The flower is generally not affected by wet weather, but ages as temperature rises.

Fragrance: Not noticeable.

Persistence: The flowers tend to hang on and dry.

Lasting quality: 3 to 6 weeks on the plant, depending on size of the bulb and the temperature; 10 days to 2 weeks as a cut flower.

REPRODUCTIVE ORGANS

Stamens:

*Anthers.*—6 in number. Arrangement: Orderly around pistil. Length: About ½ inch. Color: Pale Yellow 7B.

*Filiaments.*—About 2 inches long.

Pistils:

*Number.*—One.

*Style.*—About 2 inches long.

*Stigma.*—Color — Very Pale Yellow.

Ovary: Contained in a seed pod, about 1½ inches long and 1 inch in diameter, having 6 rows of seeds of the usual shape.

This new variety of lily plant most nearly resembles the variety "Yellow Jewel" (U.S. Plant Pat. No. 3,805). The petals of this new plant (Gold Nugget) exhibit more inward rolling of the petal edges than occurs in "Yellow Jewel" and, therefore, they appear to be smaller in size. The following chart shows a comparison of pertinent details of the two lily plants.

| | GOLD NUGGET | YELLOW JEWEL |
|---|---|---|
| A. BLOSSOM | | |
| 1. Form: | Cupped more than Yellow Jewel | More flat |
| 2. Color: | Yellow 7B | Yellow 6A |
| 3. Petals: | About 3 to 12 | |
| a. Spots: | Spots on each petal | Occasionally one spot on each petal |
| b. Shape: | Edges roll in full length of petal | Nearly flat |
| 4. Stigma Tip: | Very pale yellow in color | Maroon in color |
| 5. Buds on Pedicels | Usually one | Usually two |
| B. FLOWERING | | |
| 1. Response: | Blooms earlier than Yellow Jewel | Blooms later than Gold Nugget |
| C. PLANT | | |
| 1. Height: | 2 to 3 feet depending on age of bulb | About 20% higher than Gold Nugget |
| 2. Stem: | Begins forming aerial bulbils in leaf axils at blooming time | Does not form aerial bulbils in the leaf axils |
| 3. Stem Bulblets (under ground): | 4 to 12 at digging time | 2 to 6 at digging time |

I claim:

1. A new and distinct variety of Asiatic Hybrid lily plant substantially as herein shown and described characterized by the color, form and arrangement of its bright yellow flowers, by its profuse production of flower buds which bloom progressively to provide an extended blooming period, and by the long lasting quality of the blooms on the plant and as cut flowers.

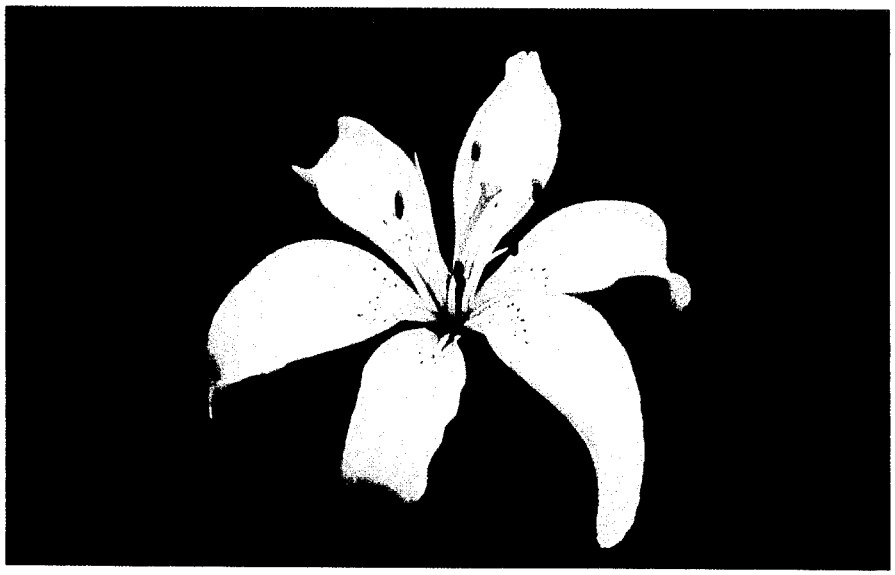
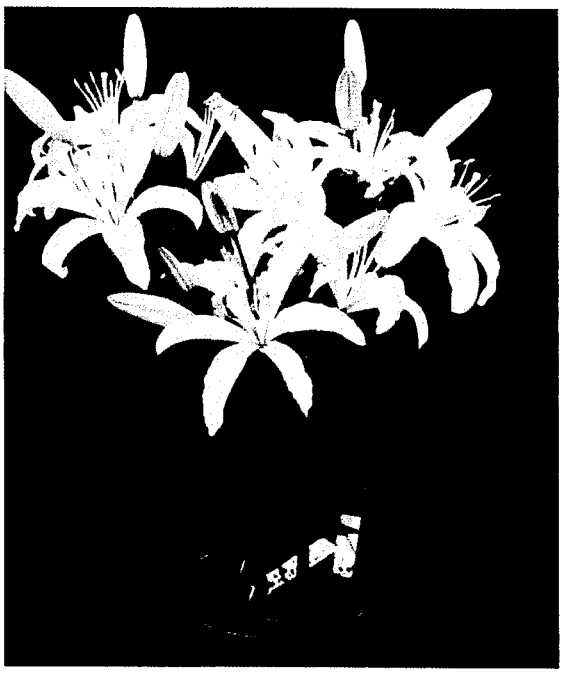

* * * * *